US00PP34391P2

(12) United States Plant Patent
van Langen

(10) Patent No.: US PP34,391 P2
(45) Date of Patent: Jun. 28, 2022

(54) ***ECHEVERIA* X *GRAPTOPETALUM* PLANT NAMED 'AMIECH2002'**

(50) Latin Name: ***Echeveria* x *Graptopetalum***
Varietal Denomination: AMIECH2002

(71) Applicant: Novoami B.V., Heerhugowaard (NL)

(72) Inventor: Gerard van Langen, Heerhugowaard (NL)

(73) Assignee: Novoami B.V., Heerhugowaard (NL)

( * ) Notice: Subject to any disclaimer, the term of this patent is extended or adjusted under 35 U.S.C. 154(b) by 0 days.

(21) Appl. No.: 17/300,670

(22) Filed: Sep. 20, 2021

(30) Foreign Application Priority Data

Jan. 4, 2021 (QZ) ..... PBR 2021/0006

(51) Int. Cl.
*A01H 5/12* (2018.01)
*A01H 6/32* (2018.01)

(52) U.S. Cl.
USPC ..... Plt./373

(58) Field of Classification Search
USPC ..... Plt./373, 263.1
CPC ... A01H 5/12; A01H 5/02; A01H 5/00; A01H 6/32; A01H 6/00
See application file for complete search history.

(56) References Cited

PUBLICATIONS

Mountain Crest Gardens, retrieved on Oct. 26, 2021, retrieved from the Internet at https://mountaincrestgardens.com/echeveria-brown-rose/, 4 pp. (Year: 2021).*

* cited by examiner

*Primary Examiner* — June Hwu
(74) *Attorney, Agent, or Firm* — Samuel R. McCoy, Jr.

(57) ABSTRACT

A new and distinct *Echeveria* x *Graptopetalum* plant named 'AMIECH2002' which is characterized by a relatively small foliage that is tightly held in a compact basal rosette, moderately glaucous foliage with a greyed-green general appearance, mature foliage that is tipped and narrowly margined with a mixture of yellow-green and grey-brown, and the stability of these characteristics from generation to generation.

4 Drawing Sheets

Latin name of the genus and species: The Latin name of the genus and species of the novel variety disclosed herein is *ECHEVERIA* x *GRAPTOPETALUM elegans* Rose (syn. *E. albicans*) x *Graptopetalum filiferum* (S. Watson) J. Whitehead.

Variety denomination: The inventive variety of *Echeveria* x *Graptopetalum* disclosed herein has been given the variety denomination 'AMIECH2002'.

CROSS REFERENCE TO RELATED APPLICATIONS

This application claims priority to the Community Plant Variety Rights application number 2021/0006, filed Jan. 4, 2021, which is herein incorporated by reference.

BACKGROUND OF THE INVENTION

Parentage: 'AMIECH2002' is an intergeneric hybrid seedling selection resulting from the controlled pollination of an *Echeveria elegans* 'Brown Rose' plant (not patented), the seed parent, with an unnamed *Graptopetalum filiferum* plant (not patented), the pollen parent. The crossing was made by the inventor in the summer of 2016 at a commercial greenhouse in Heerhugowaard, the Netherlands. In the summer of 2018, one seedling was observed which exhibited unique growth and foliage characteristics. The seedling was isolated for further evaluation in order to confirm the distinctness and stability of the characteristics first observed.

Upon confirmation of distinctness and stability, 'AMIECH2002' was selected for commercialization.

Asexual Reproduction: Asexual reproduction of the new cultivar 'AMIECH2002', by way of rooting leaf cuttings, was first initiated in the spring of 2018 at the inventor's commercial greenhouse in Heerhugowaard, the Netherlands. Through three subsequent generations, the unique features of this cultivar have proven to be stable and true to type.

SUMMARY OF THE INVENTION

The cultivar 'AMIECH2002' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIECH2002'. These characteristics in combination distinguish 'AMIECH2002' as a new and distinct *Echeveria* x *Graptopetalum* cultivar:

1. 'AMIECH2002' exhibits a small, compact basal rosette of tightly held foliage; and
2. 'AMIECH2002' exhibits relatively small, broad obovate foliage with a mucronate apex; and
3. 'AMIECH2002' exhibits juvenile and mature foliage which is covered with greyed-green epicuticular wax that gives the foliage a greyed-green appearance; and
4. 'AMIECH2002' exhibits yellow-green to green mature foliage that is narrowly margined yellow-green and tipped with a mixture of yellow-green and grey-brown.

BOTANICAL DESCRIPTION OF THE PLANT

Figure 1:
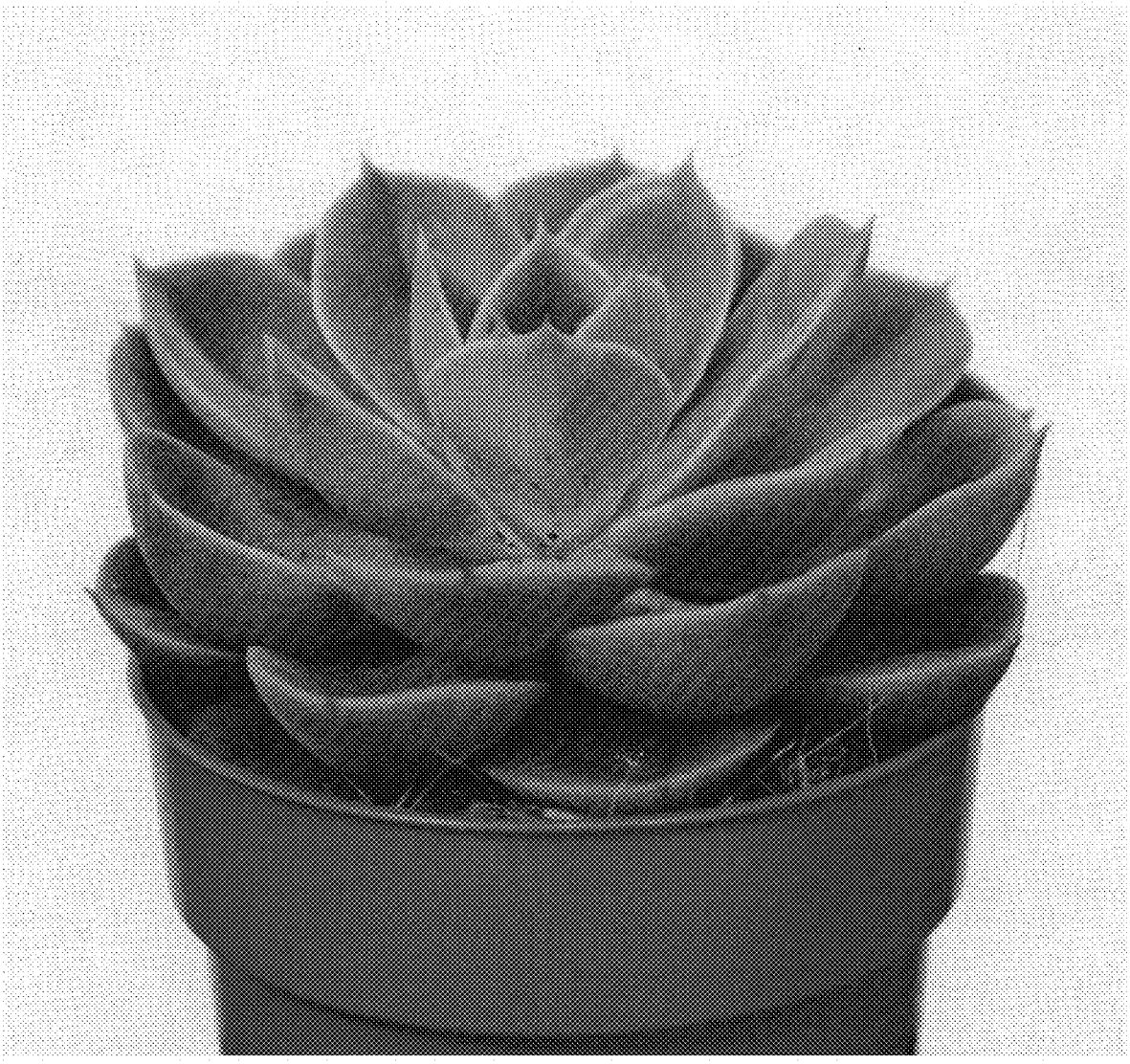
FIG. 1 illustrates, as nearly true as it is reasonably possible to make the same in color photographs of this type, an exemplary plant of 'AMIECH2002' grown in a commercial greenhouse in Heerhugowaard, the Netherlands. This plant is approximately 20 week-old, shown planted in an 8.5 cm container.
Figure 2:
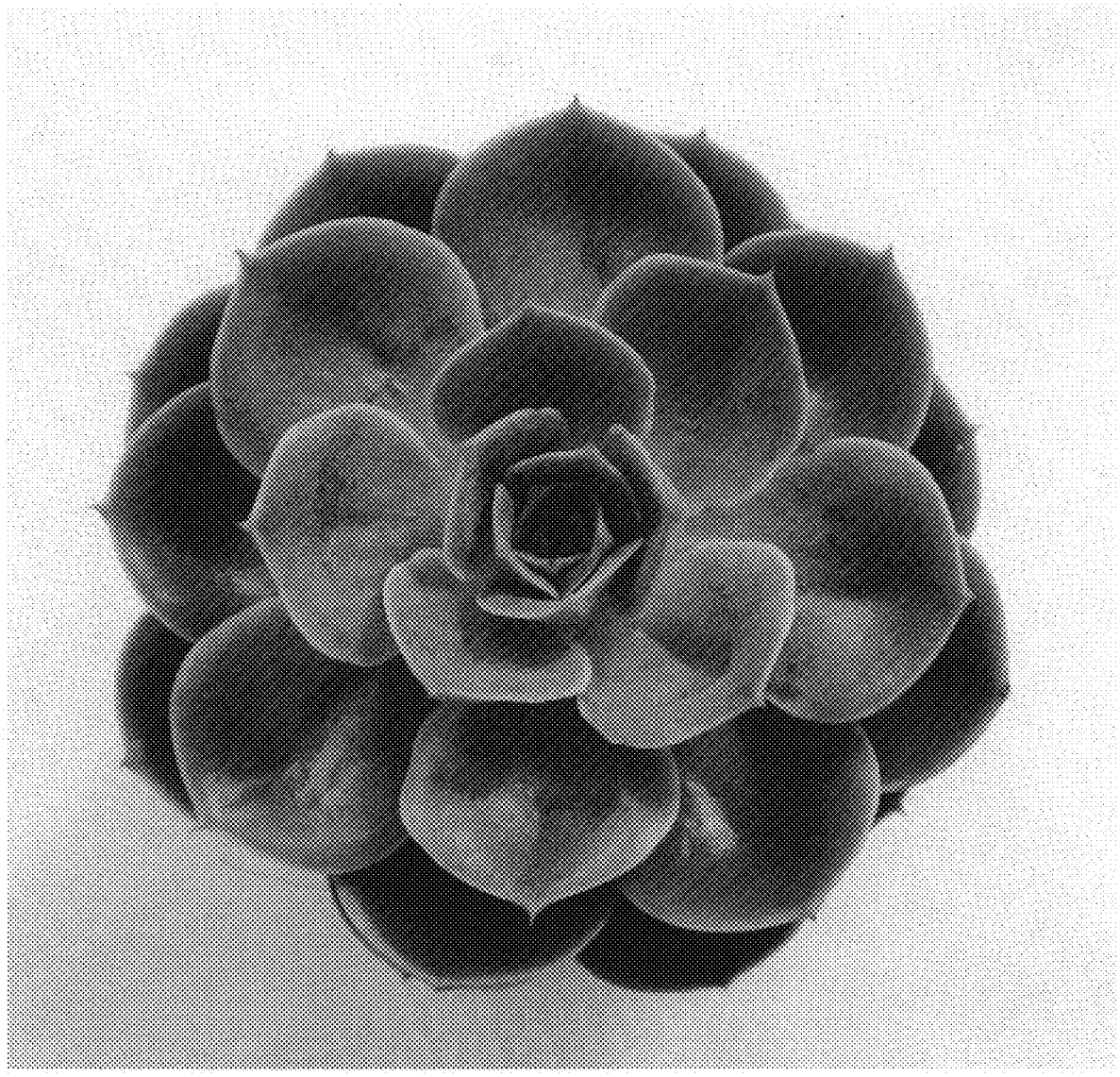
FIG. 2 illustrates, as nearly true as it is reasonably possible to make the same in color photographs of this type, the typical foliage arrangement of 'AMIECH2002'.
Figure 3:
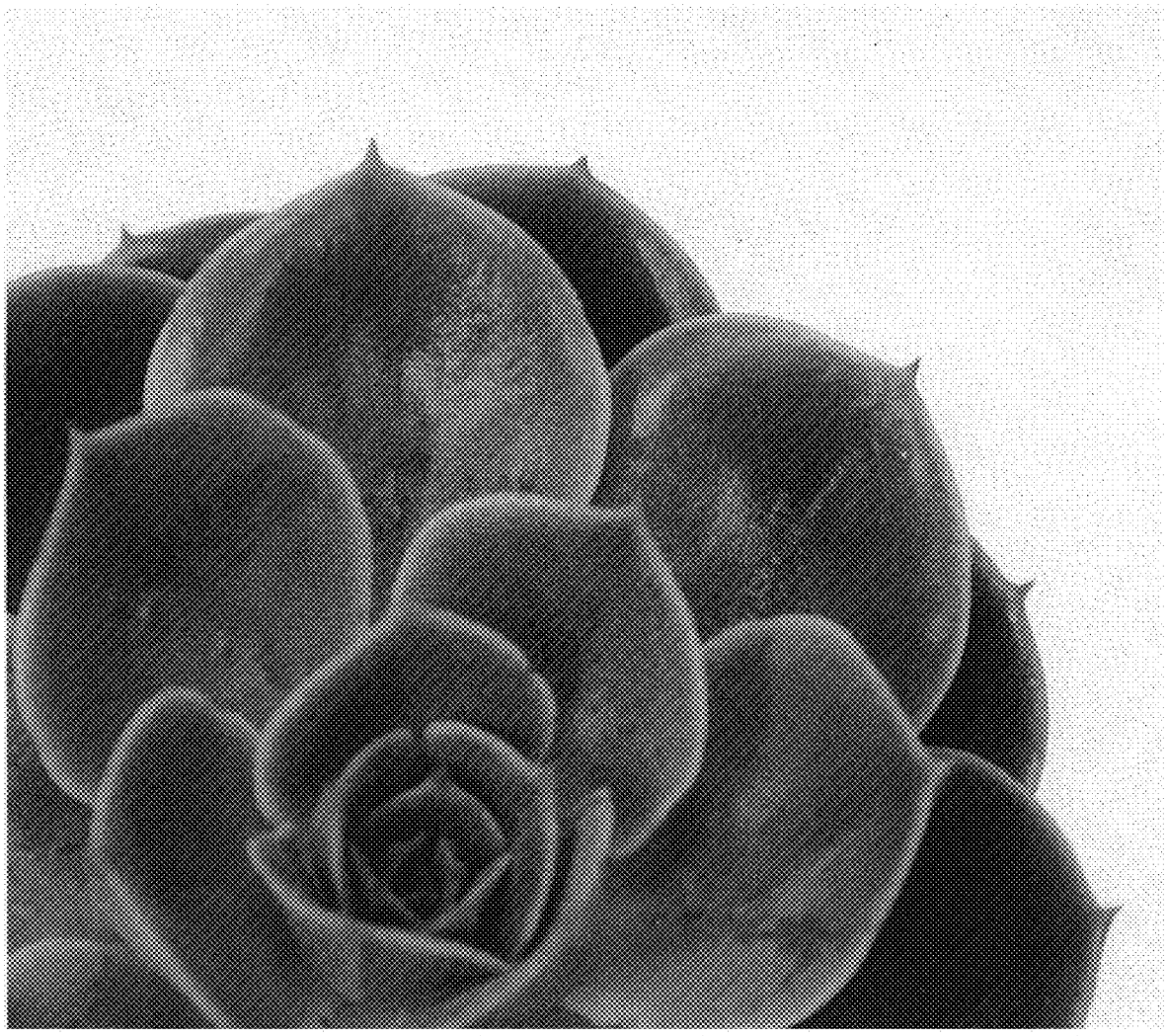
FIG. 3 illustrates; as nearly true as it is reasonably possible to make the same in color photographs of this type, the adaxial surface of the mature foliage 'AMIECH2002'.
Figure 4:
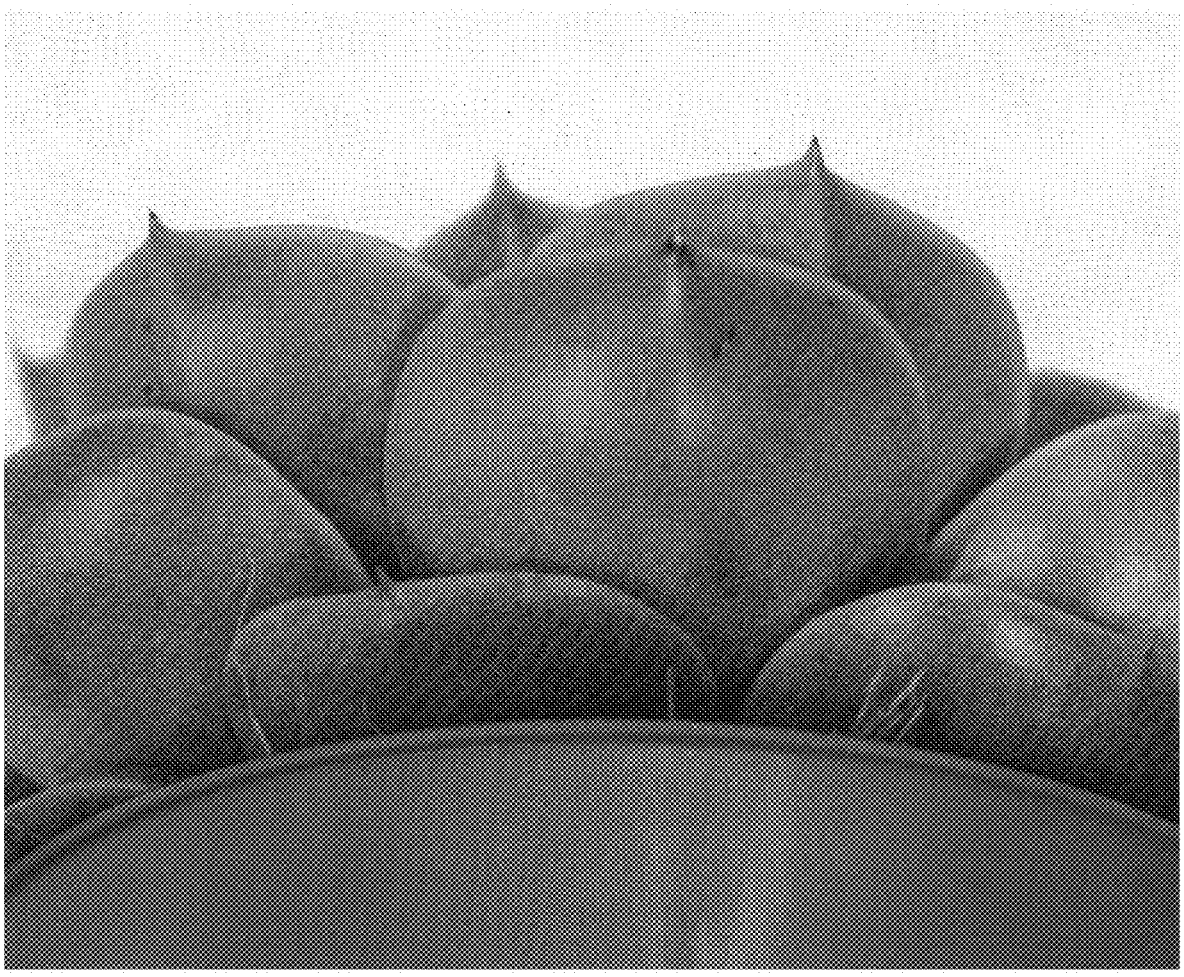
FIG. 4 illustrates, as nearly true as it is reasonably possible to make the same in color photographs of this type, the abaxial surface of the mature foliage 'AMIECH2002'.

The following observations and measurements made in June of 2021 describe averages from a sample set of six specimens of 20 week-old 'AMIECH2002' plants grown in 8.5 cm nursery containers at commercial greenhouse in Heerhugowaard, the Netherlands. Plants were produced using conventional greenhouse production protocols for *Echeveria* x *Graptoptalum* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'AMIECH2002' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'AMIECH2002' and comparisons with the parent plants and closest known comparator are provided below.

Plant description:

*Growth habit*.—Succulent perennial with foliage growing in a non-branched basal rosette.

*Plant shape*.—Flattened globular.

*Height from soil level to top of foliar plane*.—4.4 cm.

*Plant spread*.—Average of 9.7 cm.

*Plant vigor*.—Moderately vigorous.

*Propagation*.—Type — Leaf cuttings. Time to initiate rooting — Approximately 21 days at 18 degrees Celsius. Crop time — Approximately 25 weeks to produce a marketable plant in an 8.5 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Rosette.

*Division*.—Simple.

*Attachment*.—Sessile.

*Quantity*.—Approximately 35 leaves per rosette.

*Shape*.—Broad obovate.

*Dimensions*.—4.4 cm long, 3.0 cm wide, and 0.55 cm thick, on average.

*Aspect*.—Slightly concave with leaf tips slightly curled upward at an approximate angle of 20 degrees to the lamina.

*Attitude*.—Juvenile foliage at the center of the rosette is held upright; foliage becomes progressively more relaxed towards the outer whorls of mature foliage.

*Apex*.—Mucronate.

*Base*.—Cuneate.

*Margin*.—Entire; margins are not undulate.

*Pubescence, texture and luster of the adaxial surface*.—Smooth, glabrous, and moderately glaucous.

*Pubescence, texture and luster of the abaxial surface*.—Smooth, glabrous, and moderately glaucous.

*Luster of the adaxial surface*.—Moderately glossy.

*Luster of the abaxial surface*.—Moderately glossy.

*Color*.—Juvenile foliage, adaxial surface — Green, nearest to a RHS NN137A, and fading to yellow-green towards the base, nearest to RHS 145C; narrowly margined with a translucent yellow-green, nearest to RHS 147D; tipped with a slightly darker shade of yellow-green, nearest to RHS 146D. The epicuticular glaucous wax covering the leaf surface is greyed-green, nearest to RHS 189B. Juvenile foliage, abaxial surface — Greyed-green, nearest to a RHS 191A, and fading to yellow-green towards the base, nearest to RHS 145C; narrowly margined with a translucent yellow-green, nearest to RHS 145B; tipped with a slightly darker shade of yellow-green, nearest to RHS 146D. The epicuticular glaucous wax covering the leaf surface is greyed-green, nearest to RHS 189B. Mature foliage, adaxial surface — Nearest to a mixture of green and yellow-green, RHS NN137A and 147A, and fading to yellow-green towards the base, nearest to RHS 147C; narrowly margined yellow-green, nearest to RHS 144B; margins lightly suffused with a mixture of yellow-green and grey-brown towards the apex, nearest to RHS 152B and 199B; tipped with a mixture of yellow-green and grey-brown, nearest to RHS 152B and 199B. The epicuticular glaucous wax covering the leaf surface is greyed-green, nearest to RHS 189B. Mature foliage, abaxial surface — Yellow-green, nearest to RHS 147B, and fading to a lighter shade of yellow-green towards the base, nearest to RHS 147D; narrowly margined yellow-green, nearest to RHS 144B; tipped with a mixture of yellow-green and grey-brown, nearest to RHS 152B and 199B. The epicuticular glaucous wax covering the leaf surface is greyed-green, nearest to RHS 189B. Venation, adaxial surface — No visible venation. Venation, abaxial surface — No visible venation.

*Petiole*.—No petiole; leaves are sessile.

Inflorescence: No flowering has been observed to date.

COMPARISONS WITH THE PARENT PLANTS AND CLOSEST KNOWN COMPARATOR

Plants of the new cultivar 'AMIECH2002' differ from the seed parent, an *Echeveria elegans* 'Brown Rose' plant (not patented), in the following characteristics described in Table 1 below.

TABLE 1

| Characteristic | 'AMIECH2002' | 'Brown Rose' |
|---|---|---|
| Foliage margin pubescence. | Glabrous. | Ciliate. |
| General coloration of the mature foliage. | Green with greyed-green epicuticular wax with gives the foliage a greyed-green appearance. | Green and strongly suffused with greyed-red to greyed-purple. |

Plants of the new cultivar 'AMIECH2002' differ from the pollen parent, an unnamed *Graptopetalum filiferum* plant (not patented), in the following characteristics described in Table 2 below.

TABLE 2

| Characteristic | 'AMIECH2002' | The seed parent. |
|---|---|---|
| Plant size. | Larger than the seed parent. | Smaller than 'AMIECH2002'. |
| Foliage length. | Shorter than the seed parent. | Longer than 'AMIECH2002'. |

TABLE 2-continued

| Characteristic | 'AMIECH2002' | The seed parent. |
|---|---|---|
| Foliage apex. | Short mucronate tip, colored with a mixture of yellow-geen and grey-brown. | Acuminate and tipped with a fine red filament. |
| Foliage thickness. | Thinner than the seed parent. | Thicker than 'AMIECH2002'. |

COMPARISONS WITH THE CLOSEST KNOWN COMPARATOR

Plants of the new cultivar 'AMIECH2002' differ from the closest known commercial comparator, x *Pachyveria* 'AMIECH1621' (U.S. Plant Pat. No. 33,280), in the following characteristics described in Table 3 below.

TABLE 3

| Characteristic | 'AMIECH2002' | 'AMIECH1621' |
|---|---|---|
| Plant size. | Smaller than 'AMIECH1621'. | Larger than 'AMIECH2002'. |
| Foliage shape. | Broad obovate. | Narrow obovate. |
| Foliage size. | Smaller than 'AMIECH1621'. | Larger than 'AMIECH2002'. |
| General coloration of the mature foliage. | Yellow-green to green and covered with greyed-green epicuticular wax that gives the foliage a greyed-green appearance | Yellow-green to greyed-green and moderately covered with lighter greyed-green epicuticular wax that gives the foliage a blue-grey appearance. |

That which is claimed is:

1. A new and distinct variety of *Echeveria* x *Graptopetalum* plant named 'AMIECH2002', substantially as described and illustrated herein.

* * * * *